(12) United States Patent
Manzke et al.

(10) Patent No.: US 10,575,757 B2
(45) Date of Patent: Mar. 3, 2020

(54) CURVED MULTI-PLANAR RECONSTRUCTION USING FIBER OPTIC SHAPE DATA

(75) Inventors: Robert Manzke, Husberg (DE);
Raymond Chan, San Diego, CA (US);
Martin Bernardus Van Der Mark, Best (NL); Gert Wim 'T Hooft, Eindhoven (NL); Bharat Ramachandran, Morganville, NJ (US);
Laurent Verard, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1782 days.

(21) Appl. No.: 14/236,331

(22) PCT Filed: Aug. 13, 2012

(86) PCT No.: PCT/IB2012/054108
§ 371 (c)(1),
(2), (4) Date: Jan. 31, 2014

(87) PCT Pub. No.: WO2013/024418
PCT Pub. Date: Feb. 21, 2013

(65) Prior Publication Data
US 2014/0155737 A1 Jun. 5, 2014

Related U.S. Application Data

(60) Provisional application No. 61/523,930, filed on Aug. 16, 2011.

(51) Int. Cl.
*A61B 5/06* (2006.01)
*A61B 6/03* (2006.01)
(Continued)

(52) U.S. Cl.
CPC .......... *A61B 5/066* (2013.01); *A61B 1/00147* (2013.01); *A61B 1/00165* (2013.01); *A61B 5/065* (2013.01); *A61B 5/4887* (2013.01); *A61B 5/742* (2013.01); *A61B 6/032* (2013.01); *A61B 6/12* (2013.01); *A61B 6/462* (2013.01);
(Continued)

(58) Field of Classification Search
USPC ........................................................ 600/417
See application file for complete search history.

(56) References Cited

U.S. PATENT DOCUMENTS

2008/0071142 A1 3/2008 Gattani et al.
2008/0177172 A1 7/2008 John et al.
(Continued)

FOREIGN PATENT DOCUMENTS

JP 2002306403 A 10/2002
JP 2007044121 A1 2/2007
(Continued)

*Primary Examiner* — Pierre E Elisca

(57) ABSTRACT

A system and method include a shape sensing enabled device too (102) having an optical fiber (126). An interpretation module (115) is configured to receive optical signals from the optical fiber within a structure and interpret the optical signals to determine a shape of the device. An image generation module (140) is configured to receive the shape of the device, register the shape with an image volume of the structure and generate a curved Memory multi-planar reconstruction (CMPR) rendering based on the shape.

26 Claims, 5 Drawing Sheets

(51) Int. Cl.
*A61B 8/00* (2006.01)
*A61B 6/00* (2006.01)
*A61B 8/08* (2006.01)
*A61B 6/12* (2006.01)
*A61B 5/00* (2006.01)
*A61B 1/00* (2006.01)
*A61M 25/01* (2006.01)
*A61M 25/09* (2006.01)
*G01R 33/28* (2006.01)
*A61B 8/12* (2006.01)
*A61B 34/20* (2016.01)

(52) U.S. Cl.
CPC .............. *A61B 6/463* (2013.01); *A61B 6/466* (2013.01); *A61B 6/5235* (2013.01); *A61B 6/5247* (2013.01); *A61B 8/0841* (2013.01); *A61B 8/462* (2013.01); *A61B 8/463* (2013.01); *A61B 8/466* (2013.01); *A61B 8/483* (2013.01); *A61B 8/5246* (2013.01); *A61B 8/5261* (2013.01); *A61M 25/0108* (2013.01); *A61M 25/09* (2013.01); *G01R 33/285* (2013.01); *A61B 5/0035* (2013.01); *A61B 5/7425* (2013.01); *A61B 6/00* (2013.01); *A61B 6/037* (2013.01); *A61B 8/12* (2013.01); *A61B 2034/2061* (2016.02)

(56) References Cited

U.S. PATENT DOCUMENTS

| | | | |
|---|---|---|---|
| 2009/0310847 | A1 | 12/2009 | Matsuzaki et al. |
| 2010/0239140 | A1 | 9/2010 | Ruijters et al. |
| 2015/0182144 | A1* | 7/2015 | Bharat ............ A61B 8/0841 600/424 |

FOREIGN PATENT DOCUMENTS

| | | |
|---|---|---|
| JP | 2007136164 A | 6/2007 |
| JP | 2008173395 A | 7/2008 |
| JP | 2009160205 A1 | 7/2009 |
| WO | WO200133165 | 5/2001 |
| WO | 2007018289 A1 | 2/2007 |

* cited by examiner

CURVED MULTI-PLANAR RECONSTRUCTION USING FIBER OPTIC SHAPE DATA

CROSS-REFERENCE TO PRIOR APPLICATIONS

This application is the U.S. National Phase application under 35 U.S.C. § 371 of International Application Ser. No. PCT/IB2012/054108, filed on Aug. 13, 2012, which claims the benefit of U.S. Provisional Application Ser. No. 61/523, 930, filed on Aug. 16, 2011. These applications are hereby incorporated by reference herein.

This disclosure relates to medical instruments and more particularly to shape sensing optical fibers in medical applications for improving curved multi-planar reconstruction or reformatting.

Curved Multi-planar Reformatting or Reconstruction (CMPR) is a very useful tool in computed tomography (CT), e.g., dental CT, cardiac CT, industrial CT, etc. A volume is built by stacking axial slices one behind the other. CMPR involves generating perspectives for a stack of axial slices so that panoramic images and images from paraxial cuts can be generated. CMPR is commonly used for visualizing structures with curved geometry, such as dental or cardiac features. CMPR operation includes generating a multi-planar reconstruction (MPR) line on an axial (or coronal or sagittal) plane (e.g., in a two dimensional (2D) view). This may include generating a curved line along a region of interest. The CMPR can be rendered visible in a three-dimensional modality. Slices along the line can be rendered for viewing such that cross-sections or slices parallel to a selected plane are available to be individually reviewed for the region of interest. The orientation of the plane over the MPR line can change to axial, coronal or sagittal. This is achieved by selecting the appropriate view. It is possible to visualize thicker or thinner slab (slices).

CMPRs of volumetric imaging data are important to radiologists for various diagnostic purposes (e.g., vessel dimension and pathology analysis). Generating path data (e.g., the curved line) for this imaging mode can be a tedious manual task requiring selection of landmark points. The task is still difficult even if done automatically using image-based centerline or segmentation algorithms.

In accordance with the present principles, a system and method include a shape sensing enabled device having an optical fiber. An interpretation module is configured to receive optical signals from the optical fiber within a structure and interpret the optical signals to determine a shape of the device. An image generation module is configured to receive the shape of the device, register the shape with an image volume of the structure and generate a curved multi-planar reconstruction (CMPR) rendering based on the shape.

A workstation includes a shape sensing system including a shape sensing enabled medical device having at least one optical fiber and an interpretation module configured to receive optical signals from the at least one optical fiber within a structure and interpret the optical signals to determine a shape of the medical device. A curved multi-planar reconstruction (CMPR) rendering module includes an image generation module configured to receive the shape of the medical device, register the shape with an image volume of the structure. The CMPR is generated from the image volume using the shape as path information. A display for viewing the CMPR is included.

A method, comprising: collecting shape sensing data from a shape sensing device disposed within a three-dimensional structure; registering the three-dimensional structure having the shape sensing device therein with an image volume; and generating a curved multi-planar reconstruction (CMPR) image from the shape sensing data such that the shape sensing data provides a path along which image volume data is employed to provide an image of the three-dimensional structure.

These and other objects, features and advantages of the present disclosure will become apparent from the following detailed description of illustrative embodiments thereof, which is to be read in connection with the accompanying drawings.

This disclosure will present in detail the following description of preferred embodiments with reference to the following figures wherein.

Figure 1:
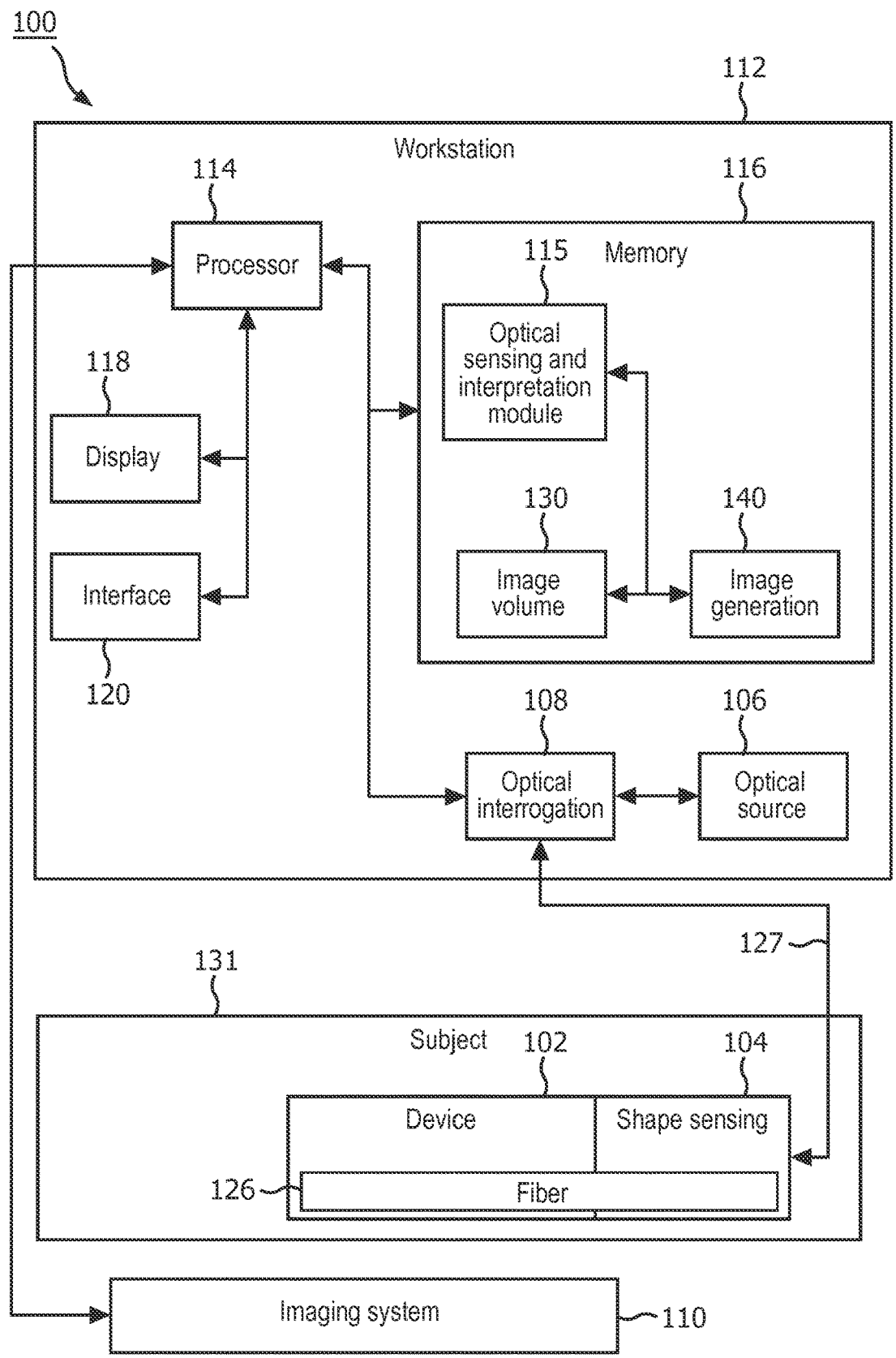
FIG. 1 is a block/flow diagram showing a system and workstation with a shape sensing system which employs shape sensed data as path data for curved multi-planar reconstruction (CMPR) imaging in accordance with one embodiment.

In accordance with the present principles, dense multi-point device tracking using fiber optic shape sensing technology, path data for curved multi-planar reconstruction (CMPR) generation during interventional procedures is made available to improve efficiency and accuracy. In particular, co-registration of an interventional device based on non-Cartesian imaging modalities, such as intravascular ultrasound (IVUS) images, with standard Cartesian datasets is not trivial. Fiber optic shape sensing CMPRs provide a method for data fusion when a fiber is integrated within the interventional device (e.g., a guide wire, catheter, etc.) and/or embedded in an imaging device (e.g., IVUS, optical coherence tomography (OCT), etc.). This is particularly useful in fusing images between non-Cartesian image modalities (e.g., (OCT, IVUS) and Cartesian imaging modalities (e.g., CT, MRI, etc.).

Non-Cartesian imaging modalities include acquisition of k-space trajectories not following the orthogonal Cartesian coordinate system (e.g., polar or radial projection imaging, etc.). Cartesian imaging modalities include acquisition of k-space trajectories following the orthogonal Cartesian coordinate system (e.g., rectilinear imaging). Examples of non-Cartesian imaging modalities include OCT, IVUS, etc. Optical coherence tomography (OCT) is an optical signal acquisition and processing method that captures micrometer-resolution, three-dimensional images from within optical scattering media (e.g., biological tissue). Optical coherence tomography is an interferometric technique, employing, e.g., near-infrared light. The use of relatively long wavelength light allows it to penetrate into the scattering medium. Depending on the properties of the light source (superluminescent diodes and ultrashort pulsed lasers), optical coherence tomography has achieved submicrometer resolution (with very wide-spectrum sources emitting over a ~100 nm wavelength range). OCT has also begun to be used in interventional cardiology to help diagnose coronary artery disease.

IVUS is a medical imaging methodology using a specially designed catheter with a miniaturized ultrasound probe attached to the distal end of the catheter. The proximal end of the catheter is attached to computerized ultrasound equipment. This permits ultrasound imaging inside blood vessels, etc., visualizing inner walls in a living body. Although illustratively described here, the non-Cartesian imaging modalities are not limited to those described and may include other types and methods.

In one embodiment, three-dimensional (3D) or 3D plus time (3D+t) imaging data is registered in an interventional setting with a shape tracking system. Each time a data frame is recorded, a CMPR is calculated along the path described by the shape tracking enabled instrument, e.g., a catheter, guide wire, etc. The CMPR is represented to the physician, reflecting a warped image of the anatomy in which the shape tracking enabled instrument is currently intersecting.

In another embodiment, focused on magnetic resonance imaging (MRI) acquisitions, real-time MRI volume parameters can be adjusted to only acquire data necessary for generation of the CMPR of the volume currently intersected by the shape tracking enabled device, potentially streamlining the acquisition time and increasing interventional imaging frame rates. This may be applied to other imaging modalities as well.

It should be understood that the present invention will be described in terms of medical instruments; however, the teachings of the present invention are much broader and are applicable to any fiber optic instruments. In some embodiments, the present principles are employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Referring now to the drawings in which like numerals represent the same or similar elements and initially to FIG. 1, a system 100 for curved multi-planar reconstruction using shape sensing enabled devices is illustratively shown in accordance with one embodiment. System 100 may include a workstation or console 112 from which a procedure is supervised and/or managed. Workstation 112 preferably includes one or more processors 114 and memory 116 for storing programs and applications. Memory 116 may store an optical sensing and interpretation module 115 configured to interpret optical feedback signals from a shape sensing device or system 104. Optical sensing module 115 is configured to use the optical signal feedback (and any other feedback, e.g., electromagnetic (EM) tracking) to reconstruct deformations, deflections and other changes associated with a medical device or instrument 102 and/or its surrounding region. The medical device 102 may include a catheter, a guidewire, a probe, an endoscope, a robot, an electrode, a filter device, a balloon device, or other medical component, etc.

A shape sensing system includes module 115 and a shape sensing device 104 mounted on or integrated into the device 102. The shape sensing system includes an optical interrogator 108 that provides selected signals and receives optical responses. An optical source 106 may be provided as part of the interrogator 108 or as a separate unit for provided light signals to the shape sensing device 104. Shape sensing device 104 includes one or more optical fibers 126 which are coupled to the device 102 in a set pattern or patterns. The optical fibers 126 connect to the workstation 112 through cabling 127. The cabling 127 may include fiber optics, electrical connections, other instrumentation, etc., as needed.

Shape sensing 104 with fiber optics may be based on fiber optic Bragg grating sensors. A fiber optic Bragg grating (FBG) is a short segment of optical fiber that reflects particular wavelengths of light and transmits all others. This is achieved by adding a periodic variation of the refractive index in the fiber core, which generates a wavelength-specific dielectric mirror. A fiber Bragg grating can therefore be used as an inline optical filter to block certain wavelengths, or as a wavelength-specific reflector.

A fundamental principle behind the operation of a fiber Bragg grating is Fresnel reflection at each of the interfaces where the refractive index is changing. For some wavelengths, the reflected light of the various periods is in phase so that constructive interference exists for reflection and, consequently, destructive interference for transmission. The Bragg wavelength is sensitive to strain as well as to temperature. This means that Bragg gratings can be used as sensing elements in fiber optical sensors. In an FBG sensor, the measurand (e.g., strain) causes a shift in the Bragg wavelength.

One advantage of this technique is that various sensor elements can be distributed over the length of a fiber. Incorporating three or more cores with various sensors (gauges) along the length of a fiber that is embedded in a structure permits a three dimensional form of such a structure to be precisely determined, typically with better than 1 mm accuracy. Along the length of the fiber, at various positions, a multitude of FBG sensors can be located (e.g., three or more fiber sensing cores). From the strain measurement of each FBG, the curvature of the structure can be inferred at that position. From the multitude of measured positions, the total three-dimensional form is determined.

As an alternative to fiber-optic Bragg gratings, the inherent backscatter in conventional optical fiber can be exploited. One such approach is to use Rayleigh scatter in standard single-mode communications fiber. Rayleigh scatter occurs as a result of random fluctuations of the index of refraction in the fiber core. These random fluctuations can be modeled as a Bragg grating with a random variation of amplitude and phase along the grating length. By using this effect in three or more cores running within a single length of multi-core fiber, the 3D shape and dynamics of the surface of interest can be followed. Other optical phenomena may also be employed, such as e.g., Brillouin scatter, etc.

An imaging system 110 may be employed for in-situ imaging of a subject 131 during a procedure. The imaging system 110 may be incorporated with the device 102 (e.g., IVUS, etc.) or may be employed externally to the subject 131. Imaging system 110 may also be employed for collecting and processing pre-operative images to map out a region of interest in the subject to create an image volume 130 for registration and with shape sensing space. An image generation module 140 is configured to receive the shape of the device, register the shape with the image volume 130 and generate a curved multi-planar reconstruction (CMPR) rendering based on the sensed shape.

Workstation 112 includes a display 118 for viewing internal images of a subject (patient) 131 including CMPRs. Imaging system 110 may include a fluoroscopy system, a computed tomography (CT) system, an ultrasonic system, a nuclear imaging system (PET, SPECT), etc. Display 118 may also permit a user to interact with the workstation 112 and its components and functions, or any other element within the system 100. This is further facilitated by an interface 120 which may include a keyboard, mouse, a joystick, a haptic device, or any other peripheral or control to permit user feedback from and interaction with the workstation 112.

In one embodiment, curved multi-planar reconstructions (CMPRs) of volumetric imaging data are needed for various diagnostic purposes (e.g., vessel dimension and pathology analysis). In accordance with the present principles, a CMPR is based upon position data provided by the shape sensing 104. The shape sensing 104 provided a continuous locus of points onto which the CMPR is generated. In particularly useful embodiments, shape sensing 104 enables the fusion or registration of a plurality of imaging modalities. The continuous locus of points provides a curved or linear line to which one or more imaging modalities can be registered. For example, non-Cartesian image modalities (e.g., OCT, IVUS) can be fused or registered with respect to Cartesian imaging modalities (e.g., CT, MRI, etc.). The fusion of multiple images taken with different imaging modalities increases accuracy and improves visualization of the images.

Figure 2:
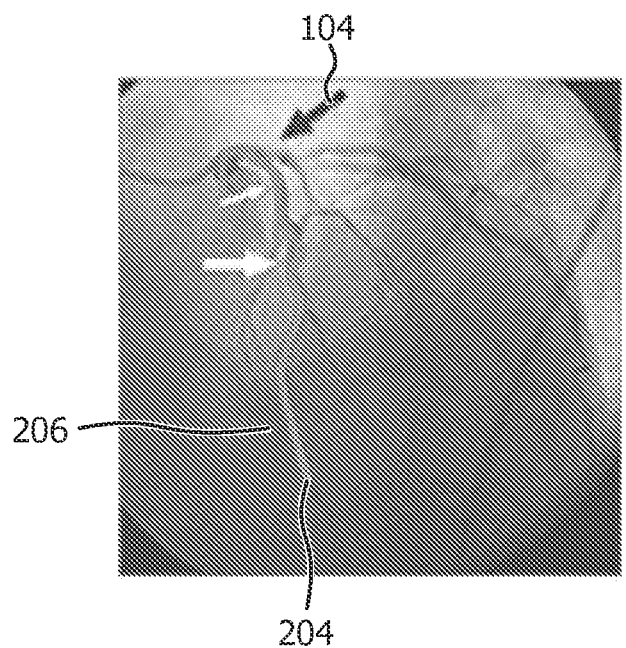
FIG. 2 is an image of a heart having a blood vessel with a shape sensing device disposed therein.

Referring to FIG. 2, in one example, an elongated device, such as a catheter, is equipped with a shape sensing optical fiber and is advanced inside a particular blood vessel 204 or other vascular structure, say e.g., within the heart 206, endoluminal structure, such as the gastro-intestinal tract, lung airway, etc. The shape sensing fiber is contorted in the shape of the blood vessel 204 or structure. The shape sensing device 104 provides path data which may be employed instead of segmenting or centerline algorithms. The shape sensing data provides a real-time snapshot of the blood vessel shape. In particular, the shape sensed fiber provides a shape which can be co-registered with pre-operative digital images of the blood vessel and/or the region of interest. In one example, a catheter-based non-Cartesian imaging modality such as intravenous ultrasound (IVUS) may have the fiber optic sensing device integrated therein. The shape of the vessel as provided by the geometry (e.g., three-dimensional shape) over time is captured from the shape sensing device and employed to register with image data collected by one or more imaging modalities (e.g., both Cartesian and non-Cartesian modalities).

Figure 3:
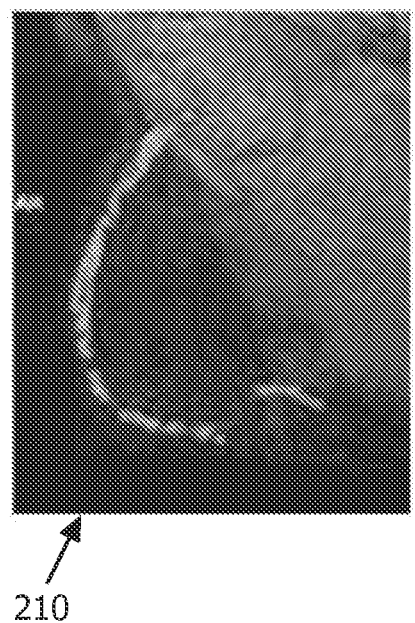
FIG. 3 is an image volume of a heart having a blood vessel corresponding to the blood vessel of FIG. 2.

Referring to FIG. 3, a three-dimensional pre-operative image 210 is illustratively shown corresponding to the blood vessel 204. The registration is performed by known registration algorithms which look for similar patterns in two data sets and register the datasets so that points of one data set match with the points of the other data set. That is, the three-dimensional spaces coincide. In one embodiment, the data sets are automatically fused when the shape sensing fiber is integrated within the imaging device (e.g., a guidewire embedded in the imaging device (such as with IVUS, OCT, etc.).

Figure 4:
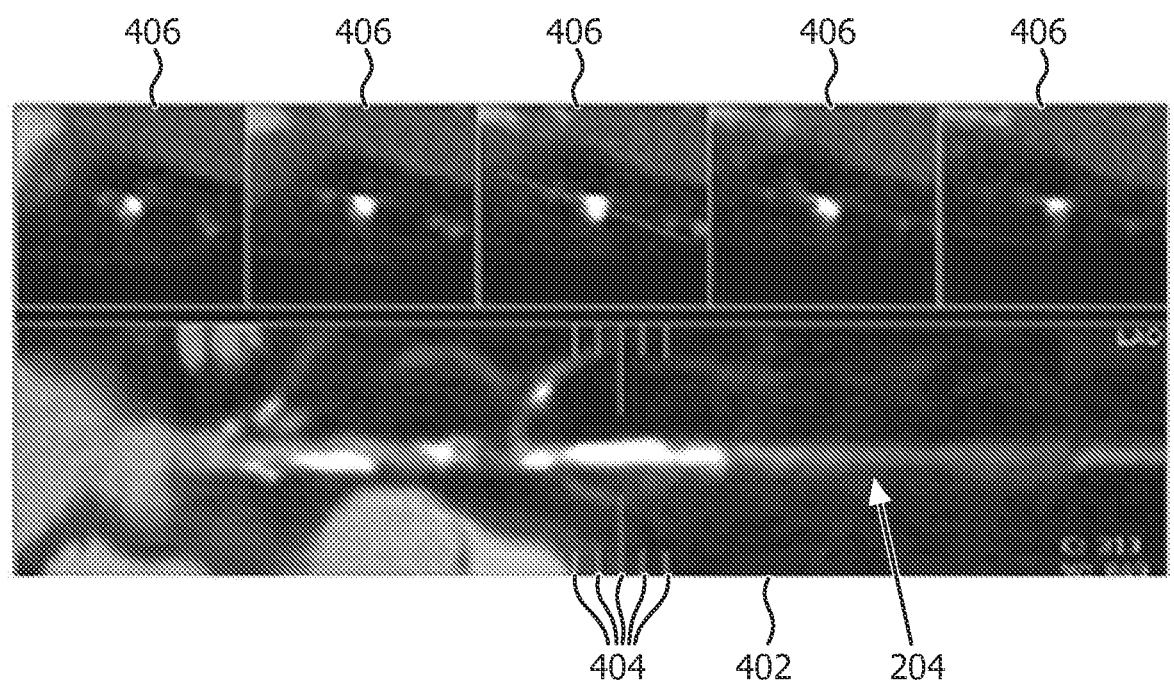
FIG. 4 is an illustrative CMPR image of the blood vessel of FIG. 3 using the shape sensing device data as a path for the CMPR image in accordance with the present principles.

Referring to FIG. 4, due to the diagnostic and therapeutic value of CMPRs within an interventional guidance context, a CMPR may be constructed based upon feedback from the shape sensing fiber. CMPR 402 includes a panoramic two-dimensional image of the blood vessel 204, which may be flattened from the three-dimensional geometry acquired during the collection of shape sensed fiber optic data. Since the shape sensed fiber optic data is co-registered or fused with the pre-operative image data, cross-section lines 404 may be indicated and employed to generate cross-sectional views 406 of internal structures of the blood vessel 204. The data of the shape sensed optical fiber is employed to calculate CMPRs of volumetric imaging data sets. The shape sensed fiber optic data delivers path information in the form of densely acquired points in five dimensions (e.g., 3D space, 1D rotation around the fiber axis, 1D time). Cross-sections 406 may be generated that are transvers through the path along vessel 204 as depicted.

Figure 5:
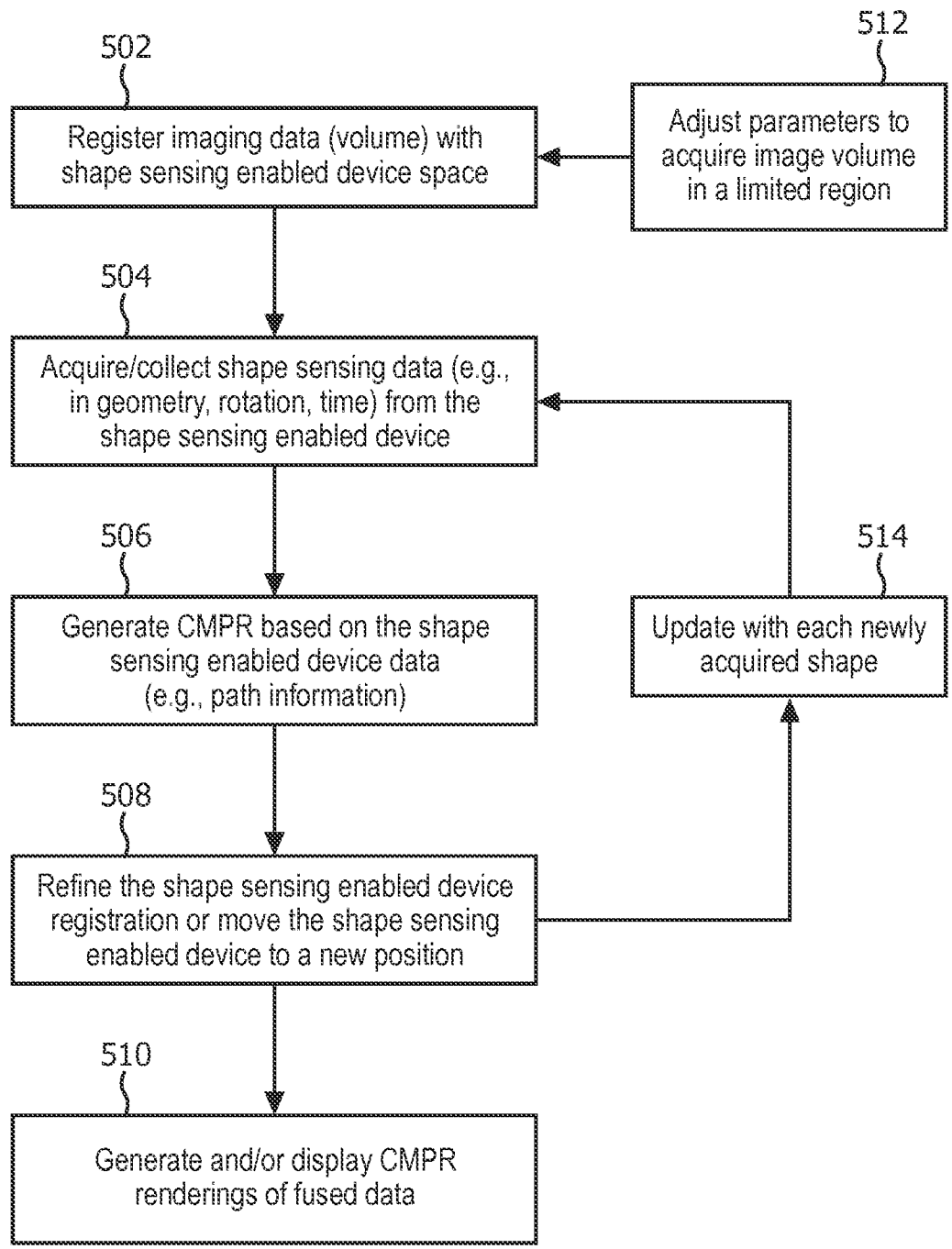
FIG. 5 is a block/flow diagram showing a system/method for employing the shape sensed data as path information for generating the CMPR in accordance with an illustrative embodiment.

Referring to FIG. 5, a block diagram is shown to describe a method for CMPR imaging in accordance with one illustrative embodiment. 3D (or 3D+time) imaging data is registered in an interventional setting with a shape tracking system in block 502. In block 504, data in multiple dimensions (e.g., up to five or more) may be continuously collected from the shape sensing enabled instrument, e.g., a catheter, a guide-wire, etc. In block 506, each time a data frame (or number of data frames) is recorded, a CMPR may be calculated along the path described by the shape sensing enabled instrument. The CMPR may be represented to the physician, reflecting a warped image of the anatomy which the shape sensing enabled instrument is currently intersecting with (e.g., located within).

Shape sensing enabled CMPR visualizations are also particularly valuable for IVUS, fractional flow reserve (FFR), OCT, or other catheter-based imaging procedures, allowing for rapid fusion of non-Cartesian imaging information with conventional Cartesian data from pre-procedural or intra-procedural modalities (e.g., computed tomography (CT), magnetic resonance images (MRI), fluoroscopy, etc.). The shape sensing enabled instrument paths in 3D can be rapidly registered in real-time with corresponding paths identified in Cartesian volumes (e.g. the coronary vasculature in a Cardiac CT volume acquisition). Fractional flow reserve (FFR) is a technique used in coronary catheterization to measure pressure differences across a coronary artery stenosis (narrowing, usually due to atherosclerosis) to determine the likelihood that the stenosis impedes oxygen delivery to the heart muscle (myocardial ischemia).

In block 508, refinement of the registration can be performed to account for any other tissue shifts between the Cartesian dataset acquisition and catheter-based imaging pullbacks (e.g., non-Cartesian datasets). A curvilinear path of the shape sensing enabled instrument permits for rapid resampling of pre-procedural or intra-procedural volumetric datasets along the instrument path at any instant in time. Alternatively, data acquired as a pullback along a curvilinear path such as volumetric IVUS or OCT data can be resampled using the real-time shape sensing enabled instrument shape information to create a volume dataset in the Cartesian imaging space of a pre-procedural or intraprocedural imaging modality. The shape sensing enabled device may be moved to a new position as part of the refinement. For any of these situations, the shape sensing enabled device based CMPRs provide dynamic co-registration and visualization of non-Cartesian catheter-based imaging datasets with Cartesian-based imaging modalities. In block 514, the CMPR may be updated for each new shape/position of the shape sensing enable device. The operation path returns to block 504 to perform the update.

For OCT, a pullback or withdrawal is rather fast, but a shape sensing 3D shape may be taken before and just after the pull back. The registration for OCT in cardiovascular applications is hampered by heart beat motions of the vessels. The data can be rescaled to a constant vessel diameter to account for this motion. An independent monitor or data from the shape sensing enabled instrument can provide information on a motion state of the organ. This information can be used to drive deformable registration between the shape sensing enabled instrument space and the volumetric data set (volume) used for generating the CMPR. In other words, the CMPR calculation process can take the motion data into account to generate temporally varying CMPRs reflecting the anatomy's current shape. If using the temporal deformation data of the shape sensing enabled instrument, temporal averaging can be used to reduce noise. Note the structure having the shape sensing device therein may include a vascular structure, or any endoluminal structure such as the gastro-intestinal tract, lung airway etc. The movement accounted for may include heart beats, peristaltic vibration, respiratory motion, etc.

In block 510, image renderings are displayed for storage or use during a procedure. The above rendering approaches can be augmented with a plurality of visualization schemes with parameter settings defined in part or entirely by information from shape sensing enabled instrument characteristics. These may include, but are not limited to, color-encoded volumetric renderings of anatomy and function, surface renderings with color-encoded maps to reflect anatomical or functional characteristics of the tissue/shape sensing enabled instrument characteristics, and translucency/opacity augmented renderings wherein the shape information is used to automatically adjust/define visualization parameters. The images may include fused images from a plurality of imaging modalities.

In another embodiment, in block 512, real-time volume parameters can be adjusted to only acquire data necessary for generation of the CMPR of the volume currently intersected by the shape enabled device. This is particularly useful with MRI modalities, which can streamline acquisition time and increase interventional imaging frame rates by collecting only needed information in a region of interest.

Figure 6:
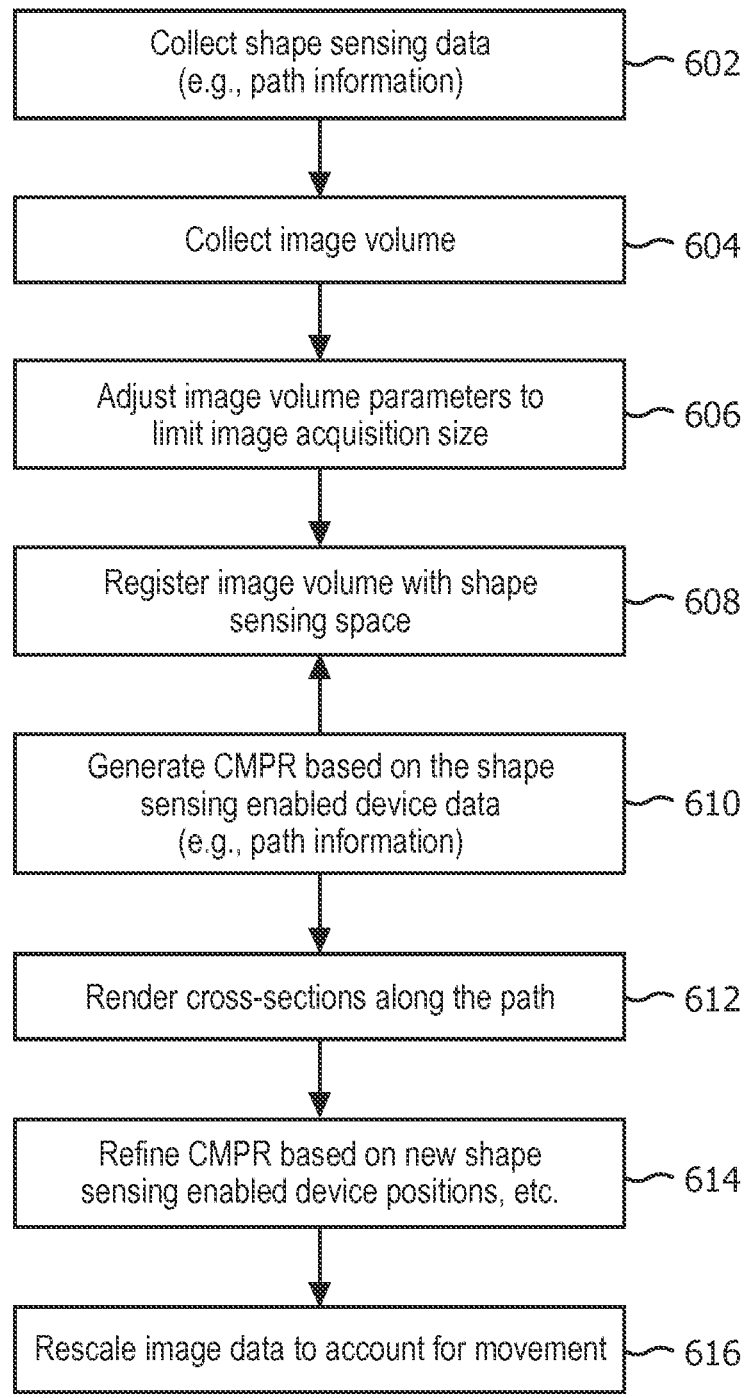
FIG. 6 is a block/flow diagram showing a system/method for employing the shape sensed data as path information for generating the CMPR in accordance with another illustrative embodiment.

Referring to FIG. 6, a method for generating a CMPR is illustratively shown in accordance with one embodiment. In block 602, shape sensing data (path information) is collected from a shape sensing device disposed within a three-dimensional structure, e.g., a vascular structure, a mechanical structure, etc. The shape sensing device may include one of an endoscope, a catheter, a guide-wire, etc.

In block 604, an image volume may be collected for the structure using one or more imaging modalities. This may be performed in advance of any procedure and may be performed at a different location and time. In block 606, image volume parameters may optionally be adjusted during an acquisition of the image volume to limit collecting of volume data to regions intersecting with the shape sensing device.

In block 608, the three-dimensional structure having the shape sensing device therein is registered with the image volume (i.e., the shape sensing space is registered with the image volume). The shape sensing device may include an imaging modality integrated therein. In such a case, the image volume and the shape sensing space are already registered. The image volume may include preoperative images of a subject or patient. The image volume may include a three-dimensional image of the structure taken by one or more of computed tomography, magnetic resonance imaging, fluoroscopy, ultrasound etc.

In block 610, a curved multi-planar reconstruction (CMPR) image is generated from the shape sensing data such that the shape sensing data provides a path along which image volume data is employed to provide an image or images of the three-dimensional structure. This may include a warped linear or unrolled two dimensional view of the structure. The view is influenced and/or based upon the path acquired by the shape sensing device for the structure. The shape sensing data may include information over time for three-dimensional space and a rotation about an axis of the shape sensing device. The view of the structure may include locations where slices or cross-sections may be taken and concurrently viewed. In block 612, the cross-sections of the structure may be rendered along the path.

In block 614, the CMPR may be refined each time a new shape is acquired for the shape sensing device or to gather additional information. In block 616, image data may be rescaled (e.g, may be part of the refinement) to account for movements in the structure. The movement may be due to heartbeats or other sources. The rescaling may include taking an average displacement or employing more sophisticated estimation tools to estimate appropriate dimensions in a CMPR view.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

Having described preferred embodiments for curved multi-planar reconstruction using fiber optic shape data (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims.

The invention claimed is:

1. A system, comprising:
a shape sensing enabled device having at least one optical fiber;
an interpretation module configured to receive optical signals from the at least one optical fiber within a structure and interpret the optical signals to determine a shape of the device; and
an image generation module configured to receive the shape of the device, register the shape with an image volume of the structure and generate a curved multi-planar reconstruction (CMPR) rendering based on the shape.

2. The system as recited in claim 1, wherein the image volume includes a three-dimensional image of the structure taken by one or more of computed tomography, magnetic resonance imaging, fluoroscopy, nuclear imaging and ultrasound.

3. The system as recited in claim 1, wherein the shape sensing enabled device includes an elongated instrument including one or more of an endoscope, a catheter and a guide-wire.

4. The system as recited in claim 1, wherein the shape sensing enabled device includes an imaging device configured to collect images at the shape sensing enabled medical device.

5. The system as recited in claim 1, wherein the shape sensing enabled device collects path information for the structure in three-dimensional space, about an axis of the at least one optical fiber and over time.

6. The system as recited in claim 1, wherein the structure includes a vascular or endoluminal structure.

7. The system as recited in claim 6, wherein the image generation module rescales image data to account for movement in the vascular or endoluminal structure.

8. The system as recited in claim 1, wherein the image generation module rescales image data to account for movements in the structure.

9. The system as recited in claim 1, wherein the shape sensing enabled device collects path information to register and fuse non-Cartesian images with Cartesian images based upon the path information.

10. A workstation, comprising:
a shape sensing system including:
a shape sensing enabled medical device having at least one optical fiber; and
an interpretation module configured to receive optical signals from the at least one optical fiber within a structure and interpret the optical signals to determine a shape of the medical device;
a curved multi-planar reconstruction (CMPR) rendering module includes:
an image generation module configured to receive the shape of the medical device, register the shape with an image volume of the structure, the CMPR being generated from the image volume using the shape as path information; and
a display for viewing the CMPR.

11. The workstation as recited in claim 10, wherein the image volume includes a three-dimensional image of the structure taken by one or more of computed tomography, magnetic resonance imaging, fluoroscopy, nuclear imaging and ultrasound.

12. The workstation as recited in claim 10, wherein the shape sensing enabled device includes an elongated instrument including one or more of an endoscope, a catheter and a guide-wire.

13. The workstation as recited in claim 10, wherein the shape sensing enabled medical device includes an imaging device configured to collect images at the shape sensing enabled medical device.

14. The workstation as recited in claim 10, wherein the path information for the structure includes three-dimensional space, rotation about an axis of the at least one optical fiber and time.

15. The workstation as recited in claim 10, wherein the structure includes a vascular or endoluminal structure.

16. The workstation as recited in claim 15, wherein the image generation module rescales image data to account for movement in the vascular or endoluminal structure.

17. The workstation as recited in claim 10, wherein the shape sensing enabled device collects path information to register and fuse non-Cartesian images with Cartesian images based upon the path information.

18. A method, comprising:
collecting shape sensing data from a shape sensing device disposed within a three-dimensional structure;
registering the three-dimensional structure having the shape sensing device therein with an image volume; and
generating a curved multi-planar reconstruction (CMPR) image from the shape sensing data such that the shape sensing data provides a path along which image volume data is employed to provide an image of the three-dimensional structure.

19. The method as recite din claim 18, further comprising rendering cross-sections of the structure along the path.

20. The method as recited in claim 19, wherein the image volume includes a three-dimensional image of the structure taken by one or more of computed tomography, magnetic resonance imaging, fluoroscopy, nuclear imaging and ultrasound.

21. The method as recited in claim 19, wherein the shape sensing device includes an elongated device including one of an endoscope, a catheter and a guide-wire.

22. The method as recited in claim 19, further comprising refining the CMPR each time a new shape is acquired for the shape sensing device.

23. The method as recited in claim 19, wherein the path for the structure includes information over time for three-dimensional space, and rotation about an axis of the shape sensing device.

24. The method as recited in claim 19, further comprising rescaling image data to account for movements in the structure.

25. The method as recited in claim 19, further comprising adjusting volume parameters during an acquisition of the image volume to limit collecting of volume data to regions intersecting with the shape sensing device.

26. The method as recited in claim 19, wherein the shape sensing enabled device collects path information to register and fuse non-Cartesian images with Cartesian images based upon the path information.

* * * * *